US00PP13320P2

(12) United States Plant Patent
Nelson et al.

(10) Patent No.: US PP13,320 P2
(45) Date of Patent: Dec. 3, 2002

(54) STRAWBERRY PLANT NAMED 'BG-633'

(75) Inventors: Steven D. Nelson, Watsonville, CA (US); Michael D. Nelson, Watsonville, CA (US); Lee W. Stoeckle, Ventura, CA (US)

(73) Assignee: Berry Genetics, Inc., Freedom, CA (US)

( * ) Notice: Subject to any disclaimer, the term of this patent is extended or adjusted under 35 U.S.C. 154(b) by 12 days.

(21) Appl. No.: 09/835,588

(22) Filed: Apr. 17, 2001

(51) Int. Cl.[7] ..... A01H 5/00

(52) U.S. Cl. ..... Plt./208

(58) Field of Search ..... Plt./208, 209

*Primary Examiner*—Bruce R. Campell
*Assistant Examiner*—Michelle Kizilkaya
(74) *Attorney, Agent, or Firm*—Foley & Lardner

(57) ABSTRACT

This invention relates to a new and distinct winter planted short day variety of strawberry known as 'BG-633'. This new variety is primarily adapted to the growing conditions of the southern coast of California. Its rounded shaped, weak to moderately glossy foliage particularly characterizes this variety. 'BG-633' produces many strongly pubescent thin runners and extremely firm cylindrical shaped fruit.

2 Drawing Sheets

SUMMARY OF THE INVENTION

The present invention relates to a new and distinct short-day strawberry variety designated as 'BG-633'. This new variety is a result of a controlled cross of 'Camarosa' (U.S. Plant Pat. No. 8,708) and 'PS-1269' (U.S. Plant Pat. No. 10,686). Plant Sciences, Inc. on behalf of Berry Genetics, Inc. performed the cross under contract. The variety is botanically known as *Fragaria ananassa.*

The seedling resulting from the aforementioned cross was asexually propagated by stolons in a nursery located in Siskiyou County, Calif., and was subsequently selected from a controlled breeding plot near Oxnard, Calif. in 1997. After its selection, the new variety was further asexually propagated in Siskiyou County, Calif. by stolons and extensively tested over the next several years in fruiting fields near Oxnard, Calif. This propagation has demonstrated that the combination of traits disclosed herein as characterizing the new variety are fixed and remain true to type through successive generations of asexual reproduction.

BRIEF DESCRIPTIONS OF THE DRAWINGS

The accompanying color photographs show typical specimens of the new variety at various stages of development as nearly true as it is possible to make in color reproductions:

FIG. 1 shows a close-up of typical leaf characteristics taken on May 13, 2000;

FIG. 2 shows a close-up of typical fruit characteristics taken on Apr. 21, 2000.

DESCRIPTION OF THE NEW VARIETY

'BG-633' primarily adapted to the climate and growing conditions of the southern coast of California. This region provides the necessary winter temperatures required for it to produce a strong vigorous plant and to remain in fruit production from January through June. The nearby Pacific Ocean provides the needed humidity and moderate temperatures to maintain fruit quality during the winter and spring production months. The following list of traits in combination define 'BG-633' as a unique variety distinguishing it from the most widely grown commercial variety in the region, 'Camarosa'.

'BG-633' is a medium sized and medium vigorous plant. When provided with optimum chilling in the nursery propagation fields prior to being dug and subsequently artificially cold stored prior to being planted the plant of the new variety is similar in size and vigor to 'Camarosa'. The plant of 'BG-633' tends to be a little more upright in growth habit as compared to 'Camarosa'. Leaf blistering of 'BG-633' tends to be medium while 'Camarosa' is medium to strong. The terminal leaflet length to width ratio of 'BG-633' is broader than long to as long as broad while 'Camarosa' is longer than broad. Leaf gloss of 'BG-633' is weak to medium while 'Camarosa' is medium. Petioles are of 'BG-633' are shorter and smaller in diameter as compared to 'Camarosa'. 'BG-633' also has fewer and shallower serrations per leaf as compared to 'Camarosa' Table 4 illustrates foliage characteristics of 'BG-633' and 'Camarosa'.

'BG-633' is capable of long season fruit production with fruit of good size and quality during the entire season when provided with optimum chilling in the nursery propagation fields and artificially cold stored prior to being planted. 'BG-633' begins fruiting early in January, similar to 'Camarosa'. 'BG-633' season average fruit size is larger than 'Camarosa' with total yields less than 'Camarosa' (Tablel). 'BG-633' also produces thicker diameter runners per plant than does 'Camarosa'. The stolon anthocyanin coloration of 'BG-633' is strong while 'Camarosa' is medium. The stolon pubescence of 'BG-633' is strong and mostly perpendicular to the stolon while 'Camarosa' is medium and mostly parallel to the stolon.

The fruit of 'BG-633' is mostly cylindrical in shape with some longitudinal creases and irregular shapes. It has excellent skin firmness and good overall appearance. See Table 3 for fruit quality performance ratings. The fruit ratio of length to width of 'BG-633' is slightly longer than broad while 'Camarosa' is much longer than broad. 'BG-633' has an absent or vary narrow band without achenes under the calyx as compared to 'Camarosa' which has a medium band. Fruit gloss of 'BG-633' is weak while 'Camarosa' is medium. The insertion of achenes of 'BG-633' is level with the surface while 'Camarosa' is typically below the surface. The attitude of the calyx segments of 'BG-633' is typically collapsing to spreading while 'Camarosa' is typically reflexed. Table 2 illustrates fruit characteristics of 'BG-633' and 'Camarosa'.

The inflorescence position of the flowers relative to the foliage of 'BG-633' is typically level with to above the foliage while 'Camarosa' is typically level with to below the foliage. 'BG-633' typically has moderate anthocyanin coloration to the inflorescence while 'Camarosa' is light. The pubescence of the inflorescence of 'BG-633' is medium to strong while 'Camarosa' is medium to weak. See Table 5 for inflorescence characteristics. The flower size of 'BG-633' is medium to large while 'Camarosa' is large. 'BG-633' typically has fewer petals per flower than does 'Camarosa'. See Table 6 for flower characteristics.

For identification a series of molecular markers have been determined for this new variety.

SPECIFIC DESCRIPTION OF THE NEW VARIETY

Unless otherwise noted, this detailed description is based on observations taken during the 2000-growing season in Oxnard, Calif. These measurements and ratings were made from plants dug from a high-elevation nursery located in Siskiyou County, Calif. during the first week in October 1999 and planted 3 days later in Oxnard, Calif. Yield observations are averaged from data collected during the 1999 and 2000 growing season. The characteristics of the new variety may vary in detail, depending upon variations in environmental factors, including weather (temperature, humidity and light intensity), day length, soil type and location. 'BG-633' has not been observed under all possible environmental conditions. Color terminology follows the Munsell Book of Colors, Munsell Color, Baltimore, Md. (1976).

Fruit Characteristics

'BG-633' fruit, fruit production and runner production (fruiting field) characteristics as compared to those of 'Camarosa'.

TABLE 1

1999–2000 average market fruit yield, fruit size and runner production characteristics from plants harvested from January through May, 1999 and 2000 of 'BG-633' dug from a high elevation nursery (Macdoel, Calif.) during the first week of October and planted 4–5 days later and compared with 'Camerosa' in Oxnard, Calif.

| Cultivar | 1999 Total Fresh* Yield GM/PL | 2000 Total Fresh* Yield GM/PL | 1999–2000 Average Fresh* Yield GM/PL | 1999–2000 Average Fruit Size Fresh Fresh GRM | 1999–2000 Average Runners/PL |
|---|---|---|---|---|---|
| 'BG-633' | 790 | 718 | 754 | 25.3 | 1.9 |
| 'Camarosa' | 876 | 799 | 837 | 22.8 | 0.4 |

TABLE 2

Comparison of secondary fruit characteristics of 'BG-633' and 'Camerosa' from Oxnard, Calif., April 7, 2000.

| Character | 'BG-633' | 'Camerosa' |
|---|---|---|
| Munsell Color | 7.5R 3/8 to 3/10 | 5R 3/8 to 3/10 |
| Fruit Length | | |
| mean (cm) | 3.9 | 4.5 |
| range | 3.5–4.4 | 4.1–5.1 |
| Fruit Width | | |
| mean (cm)* | 3.6 | 3.2 |
| range | 3.2–4.1 | 2.8–3.5 |

TABLE 2-continued

Comparison of secondary fruit characteristics of 'BG-633' and 'Camerosa' from Oxnard, Calif., April 7, 2000.

| Character | 'BG-633' | 'Camerosa' |
|---|---|---|
| Fruit Length/Width Ratio | 1.10 | 1.40 |
| Calyx Diameter | | |
| mean (cm) | 4.4 | 4.7 |
| range | 3.5–5.0 | 3.7–5.6 |

*Width is measured across the widest part of the berry, typically across the shoulders

TABLE 3

Comparison of 1998–2000 fruit quality characteristics of 'BG-633' and 'Camerosa' from Oxnard, Calif.*

| Character | 'BG-633' | 'Camerosa' |
|---|---|---|
| Skin Firness | 8.7 | 9.0 |
| Fruit Appearance | 7.5 | 7.0 |
| Fruit Gloss | 6.8 | 7.6 |

*Results are averaged from 3 years of replicated holding test performed from January through May 1998–2000. (Ratings are based on a scale from 1–10; the higher the rating, the stronger and the more attractive and glossy the berry).

Fruit characteristics are taken from secondary fruit on a first year planting.

Fruit:

*Ratio of length/width.*—Slightly longer than broad.
*Size.*—Large to very large (See Table 2).
*Predominant shape.*—Almost cylindrical to cordiform.
*Difference in shapes between primary and secondary fruit.*—Moderate to marked.
*Band without achenes.*—Absent or very narrow.
*Unevenness of surface.*—Medium.
*Color.*—Red (75R 3/8 to 3/10).
*Evenness of color.*—Slightly uneven.
*Glossiness.*—Weak.
*Insertion of achenes.*—Level with the surface.
*Insertion of calyx.*—In the basin to level.
*Attitude of the calyx segments.*—Collapsing to spreading.
*Size of calyx in relation to fruit diameter.*—Slightly larger.
*Adherence of calyx (when fully ripe).*—Strong.
*Firmness of skin.*—Firm to very firm.
*Firmness of flesh.*—Firm to very firm.
*Color of flesh.*—Light red to medium red.
*Distribution of red color of the flesh.*—Marginal and central.
*Hollow center.*—N/A.
*Time of flowering (50% of plants at first flower).*—Very early.
*Time of ripening (50% of plants with ripe fruit).*—Very early.
*Type of bearing.*—Not remontant.

Plant Characteristics

Plant characteristics are based upon plants planted with optimum field chilling and subsequent optimum artificial cold storage.

Plant:
*Size*.—Medium.
*Habit*.—Globose to flat globose.
*Density*.—Medium.
*Vigor*.—Medium.
Stolons:
*Number*.—Many.
*Anthocyanin coloration*.—Strong.
*Thickness*.—Thin.
*Pubescence*.—Strong.

Foliage Characteristics

'BG-633' foliage characteristics as compared to those of 'Camarosa'.

TABLE 4

Comparison of leaf characteristics of 'BG-633' and 'Camerosa' from Oxnard, Calif., April 7, 2000.

| Character | 'BG-633' | 'Camerosa' |
|---|---|---|
| Munsell Color (upper surface) | 5GY 3/4 to 3/6 | 5GY 3/4 to 3/6 |
| Terminal Leaflet Length | | |
| mean (cm) | 6.0 | 6.5 |
| range | 4.5–7.0 | 5.7–7.3 |
| Terminal Leaflet Width | | |
| mean (cm) | 5.6 | 6.7 |
| range | 4.8–6.8 | 5.5–8.1 |
| Terminal Leaflet ratio (L/W) | 1.07 | 0.97 |
| Petiole Length | | |
| mean (cm) | 12.4 | 16.6 |
| range | 10.0–15.0 | 15.3–18.3 |
| Petiole Width | | |
| mean (mm) | 3.0 | 3.9 |
| range | 2.5–3.9 | 3.0–5.0 |
| Petiolule Length | | |
| mean (mm) | 5.5 | 7.3 |
| range | 3–11 | 5–10 |
| Serrations/Leaf | 18.3 | 19.8 |
| Serration Depth | | |
| mean (mm) | 4.7 | 5.4 |
| range | 3.8–5.5 | 4.2–6.2 |

Foliage characteristics are taken from a fully mature tri-foliate during mid season.

Foliage:
*Color of upper surface*.—Light green to medium green.
*Shape in cross section*.—Slightly concave to flat.
*Blistering*.—Medium.
*Glossiness*.—Weak to medium.
Terminal leaflet:
*Size*.—Medium (See Table 4).
*Length/width ratio*.—Broader than long to as long as broad.
*Shape of base*.—Obtuse.
*Shape of incision of margins*—Serrate.
*Depth of serrations*.—Medium.
Petiole:
*Pubescence*.—Moderate to heavy.
*Anthocyanin coloration of stipule*.—N/A.
*Attitude of hairs*.—Slightly outward.
*Length*.—Medium to short (See Table 4).
*Thickness*.—Medium to thin.

Flowers and Inflorescences

'BG-633' inflorescence and flower characteristics as compared to those of 'Camarosa'.

TABLE 5

Comparison of inflorescence characteristics of 'BG-633' and 'Camerosa' from Oxnard, Calif., April 7, 2000.

| Character | 'BG-633' | 'Camerosa' |
|---|---|---|
| Primary Pedicel Length | | |
| mean (cm) | 15.4 | 16.8 |
| range | 12.0–18.5 | 12.0–19.0 |
| Primary Pedicel Width | | |
| mean (cm) | 3.0 | 3.2 |
| range | 2.6–3.4 | 2.8–4.2 |
| Secondary Pedicel Length | | |
| mean (cm) | 15.3 | 14.3 |
| range | 13.0–18.5 | 10.0–17.3 |
| Secondary Pedicel Width | | |
| mean (cm) | 2.6 | 2.9 |
| range | 2.3–3.4 | 2.5–3.5 |

TABLE 6

Comparison of secondary flower characteristics of 'BG-633' and 'Camerosa' from Oxnard, Calif., April 7, 2000.

| Character | 'BG-633' | 'Camerosa' |
|---|---|---|
| Flower Diameter | | |
| mean (cm) | 2.6 | 3.8 |
| range | 2.3–3.2 | 3.2–4.5 |
| Petal Length | | |
| mean (mm) | 1.1 | 1.1 |
| range | 1.0–1.2 | 1.0–1.2 |
| Petal Width | | |
| mean (mm) | 1.0 | 1.1 |
| range | 1.0–1.1 | 1.0–1.2 |
| Petal L/W Ratio | 1.04 | 1.00 |
| Petals/Flower | 5.3 | 6.4 |

Inflorescence characteristics are taken from a fully mature plant during mid season. Flower characteristics are taken from a secondary flower during mid season at full maturity:

Inflorescence:
*Position relative to foliage*.—Level with to above.
*Secondary pedicel length*.—Long.
*Secondary pedicel width*.—Medium to thin.
*Pubescence*.—Medium to strong.
*Anthocyanin*.—Moderate.
Flowers:
*Color*.—White.
*Size*.—Medium to large.
*Size of calyx relative to corolla*.—Larger.
*Relative position of petals* (*observed on flowers with 5 to 6 petals*).—Free to touching.
*Length/width ratio*.—Longer than broad.

Pest Reactions

This new variety may not be resistant to any of the known insects, diseases or viruses common in California. It is known to be susceptible to the two-spotted spider mite, aphid and flower thrips. It is also known to be susceptible to Grey fruit mold, powdery mildew and angular leafspot. The susceptibility of the new variety to any of the virus complexes of California has not been determined.

We claim:

1. A new and distinct strawberry variety as herein described and illustrated by the characteristics set forth above.

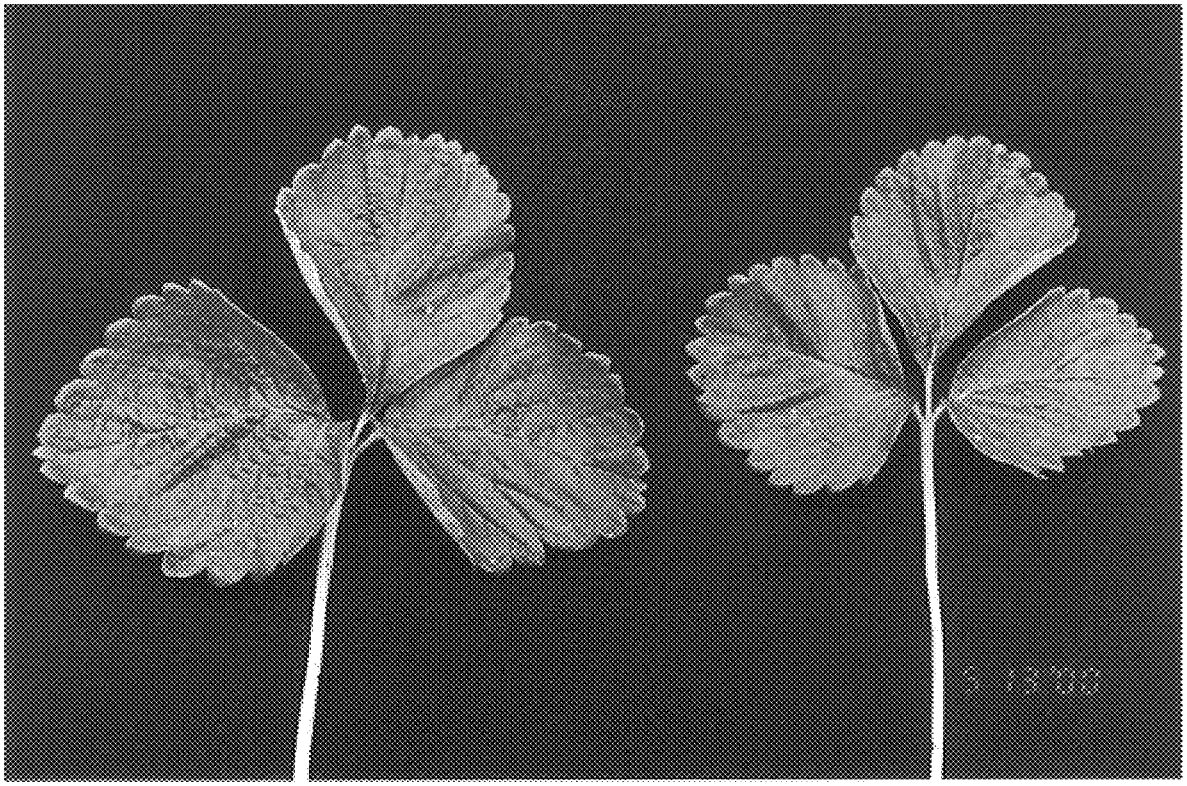

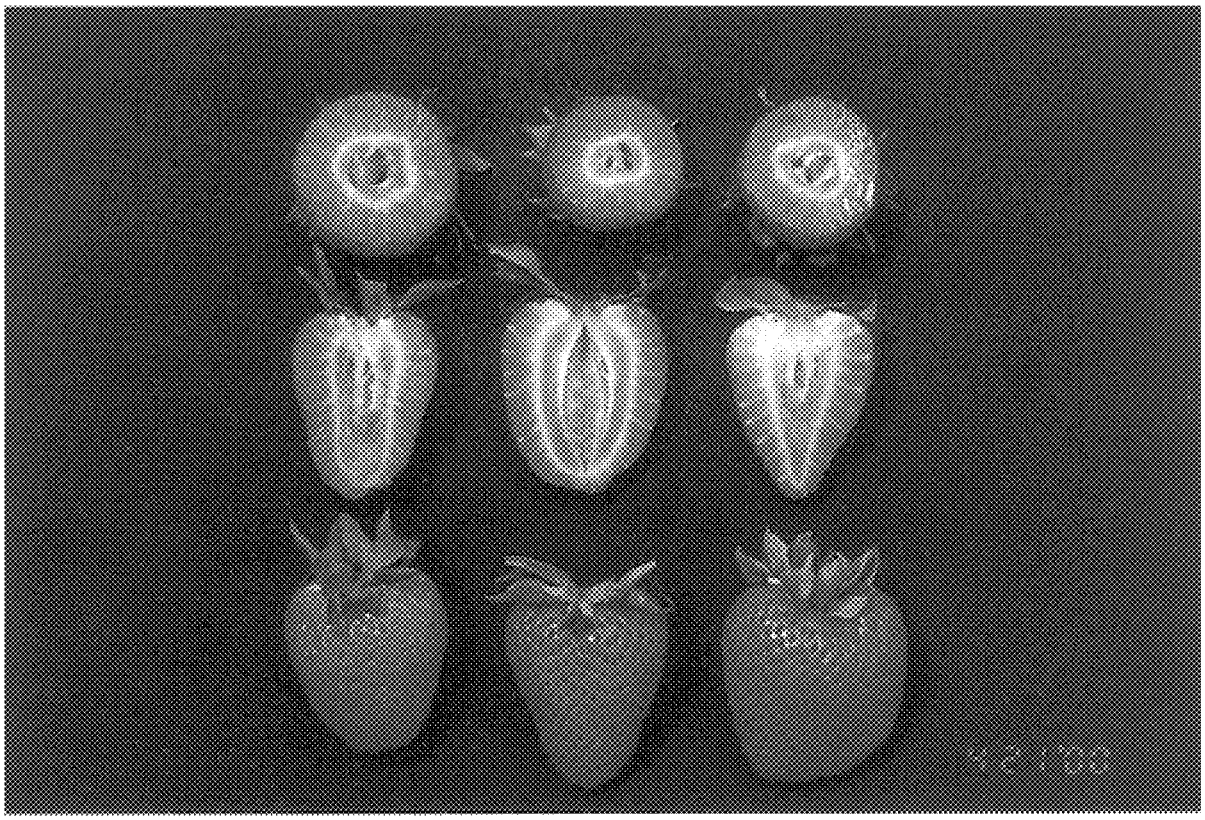

* * * * *